(12) United States Patent
Kawabata et al.

(10) Patent No.: US 6,238,408 B1
(45) Date of Patent: May 29, 2001

(54) BALLOON CATHETER

(75) Inventors: Takashi Kawabata, Tokyo; Masaru Uchiyama; Koichi Sakai, both of Kanagawa, all of (JP)

(73) Assignee: Nippon Zeon Co., Ltd., Tokyo (JP)

( * ) Notice: Subject to any disclaimer, the term of this patent is extended or adjusted under 35 U.S.C. 154(b) by 0 days.

(21) Appl. No.: 09/403,481

(22) PCT Filed: Apr. 22, 1998

(86) PCT No.: PCT/JP98/01838

§ 371 Date: Oct. 21, 1999

§ 102(e) Date: Oct. 21, 1999

(87) PCT Pub. No.: WO98/48863

PCT Pub. Date: May 11, 1998

(30) Foreign Application Priority Data

Apr. 25, 1997 (JP) .................................................. 9-123591

(51) Int. Cl.[7] .................................................. A61M 29/00
(52) U.S. Cl. .............................................. 606/192; 604/96
(58) Field of Search ............ 604/96, 101; 606/192–194; 264/515, 171.28; 428/35.6, 35.7, 36.6, 36.91, 36.8, 36.9

(56) References Cited

U.S. PATENT DOCUMENTS

| | | | | |
|---|---|---|---|---|
| 5,441,488 | * | 8/1995 | Shimura et al. | 604/265 |
| 5,478,320 | * | 12/1995 | Trotta | 604/96 |
| 5,620,649 | * | 4/1997 | Trotta | 264/515 |
| 5,670,558 | * | 9/1997 | Onishi et al. | 523/112 |
| 5,994,244 | * | 11/1999 | Fujiwara et al. | 442/365 |

FOREIGN PATENT DOCUMENTS

| | | |
|---|---|---|
| 0556034 | 8/1993 | (EP) . |
| 5-300939 | 11/1993 | (JP) . |
| 7-118431 | 5/1995 | (JP) . |
| 7-157508 | 6/1995 | (JP) . |
| 8-196620 | 8/1996 | (JP) . |

* cited by examiner

Primary Examiner—Manuel Mendez
(74) Attorney, Agent, or Firm—Dinsmore & Shohl LLP

(57) ABSTRACT

A balloon-tip catheter having a balloon formed from a polymeric material in the vicinity of the tip of a catheter, wherein the polymeric material forming the balloon comprises a polyolefin obtained by polymerization using a metallocene catalyst.

12 Claims, 1 Drawing Sheet

BALLOON CATHETER

DESCRIPTION

1. Technical Field

The present invention relates to a balloon-tip catheter, and particularly to a balloon-tip catheter having a balloon high in strength, excellent in flexibility, processability, shapeability, retention of shape, stability and fusion-bonding ability to a catheter. The balloon-tip catheter according to the present invention is particularly suitable for use as a balloon-tip catheter for dilation for dilating a living organ or coeloma such as a vessel.

2. Background Art

A balloon-tip catheter is a tube provided with a balloon on its tip, and the balloon may be inflated or deflated without drawing out the catheter after insertion thereof. When the balloon-tip catheter is inserted into a vessel to inflate the balloon, the inflated balloon is propelled by blood, so that the catheter is easily passed through the vessel. A vessel, through which the blood freely flows when the balloon is deflated, may also be occluded by inflating the balloon.

Balloon-tip catheters are used in, for example, ① arterial embolization and thrombectomy, ② venous thrombectomy, ③ dilation of a constricted artery, ④ vascular embolization and vascular occlusion, ⑤ removal of foreign matter in a vessel, etc., and are classified into, for example, balloon-tip catheters for arterial thrombectomy, balloon-tip catheters for occlusion, balloon-tip catheters for vasodilation, etc. according to the respective uses and application sites thereof.

In recent years, medical techniques have trended toward low invasive treatment against the human body. Among the balloon-tip catheters, an application range of the balloon-tip catheters for dilation for dilating living organs or coelomae has expanded in keeping with that. In general, the balloon-tip catheters for dilation have a structure that a balloon 2 is arranged in the vicinity of the tip of a catheter 1 as illustrated in FIG. 1. The balloon 2 may be inflated by introducing a gas under pressure into the balloon 2 through an opening provided in the catheter 1 or deflated by drawing the gas out of the balloon 2. The catheter 1 is generally equipped with various parts such as a side arm adapter 3 and an adapter 4.

In order to dilate a constricted artery, the outside of the body is first connected to an artery to be dilated by means of a vessel puncturing device called a sheath introducer under local anesthesia, a sheath serving as a passageway of a catheter is inserted into the artery, and a fine catheter is put in the artery through the sheath. A pressure-resistant balloon-tip catheter for dilation is then inserted into the constricted part, and the balloon is inflated, thereby pressing the hypertrophic tunica intima causing atheromatous degeneration against the tunica externa to dilate the lumen. This method is called percutaneous transluminal artery angioplasty and yields satisfactory results. The method is applied to, for example, a coronary artery, a renal artery, an external iliac artery, a femoral artery, etc. This treating method can greatly relieve patient's stress and also has an economical advantage. Accordingly, the constriction of a coronary artery or the like is often treated by a vasodilative operation making use of a balloon-tip catheter for vasodilation in place of a coronary artery bypass operation or the like previously performed.

The application range of the balloon-tip catheters for dilation is expanded making good use of their merits. Correspondingly, the balloon-tip catheters for dilation are also required to have high properties. The balloon-tip catheters for dilation are required, for example, ① to be able to treat the constriction of a peripheral coronary artery, ② to easily insert into a curved vessel, ③ to have a strong dilation pressure, and to ④ safely dilate a vessel.

More specifically, (1) it is required to be able to treat the constriction of a more peripheral coronary artery than before using a balloon-tip catheter for vasodilation. In order to meet this requirement, formation of a balloon of low profile (reduction in the projected area of the balloon in a longitudinal direction) is required. Therefore, a balloon of thinner wall and higher strength than before is required. (2) Cases of an intravascular operation, in which a balloon-tip catheter for dilation is inserted into a curved vessel, increase. In order to insert the catheter into the curved vessel with ease, the balloon is required to be flexible and have trackability. (3) A stent is often left in a coeloma for support during anastomosis or after the anastomosis, or ensuring the communication of the coeloma easy to constrict. In keeping with that, the balloon is required to have a stronger dilation pressure. (4) As the intravascular operation is frequently performed, it is required to be able to safely dilate a vessel using a balloon-tip catheter for dilation. In order to meet this requirement, the balloon is required to have a compliance (i.e., rate of change in the diameter of the balloon inflated to the dilation pressure of the balloon) within a proper range and high breaking strength.

Polyethylene resins have heretofore been principally used as materials of the balloon-tip catheters for dilation because they are comparatively good in processability and balance among their properties. However, the polyethylene resins heretofore used have involved a problem that they cannot fully meet the requirements as the requirement level against the properties of the balloon-tip catheters for dilation is heightened. The conventional balloon made of low density polyethylene (LDPE) is insufficient in both strength and flexibility. Even when a linear low density polyethylene (LLDPE) is used in place of LDPE, its improving effect on strength is a little, and only a balloon poor in flexibility can be obtained. Even when a balloon made of a polyethylene resin is crosslinked by electron beam crosslinking, water crosslinking or the like, any balloon excellent in balance among strength, flexibility, compliance upon inflation of the balloon, etc. cannot be obtained.

The balloon-tip catheter for dilation is shaped into a fixed form that a balloon is wound around a catheter in order to facilitate its insertion into and extraction from a coeloma such as a vessel, and the fixed form is often retained while the balloon is deflated under reduced pressure. However, the balloon made of the conventional polyethylene resin has been insufficient in shapeability and retention of shape. Balloons making use of a polyamide resin or polyester resin have also been known. However, it is difficult to obtain a balloon excellent in balance between strength and compliance.

As described above, various resin materials have heretofore been investigated as materials for forming a balloon of a balloon-tip catheter for dilation. However, there has not been yet obtained any material which can meet the above-described properties highly required.

DISCLOSURE OF THE INVENTION

It is an object of the present invention to provide a balloon-tip catheter having a balloon which is high in strength, excellent in flexibility, easy to shape the balloon when it is folded, good in setting ability, has a compliance within a proper range when it is inflated, and moreover is excellent in processability, retention of shape and fusion-bonding ability to a catheter.

The present inventors have carried out an extensive investigation with a view toward overcoming the above-described problems involved in the prior art. As a result, it has been found that a polyolefin obtained by polymerization using a metallocene catalyst is used, thereby obtaining a balloon-tip catheter having good various properties. It has also been found that when an ethylene-α-olefin copolymer having specific physical properties is selectively used as the polyolefin, a balloon-tip catheter, which can fully satisfied such highly required properties as described above and is suitable for use as a balloon-tip catheter for dilation in particular, can be provided.

Recently, various kinds of polyethylene resins obtained by using a metallocene catalyst have come to be provided. Since the active site of the metallocene catalyst is single, a polyolefin having even molecular weight and composition and high impact strength and transparency can be provided. In the case of, for example, an ethylene-α-olefin copolymer, polyethylene resins greatly different in density and performance can be provided by using the metallocene catalyst and changing the kind and copolymerization proportion of an α-olefin as a comonomer. The use applications of the polyolefins obtained by polymerization using the metallocene catalyst have heretofore been mainly developed into fields of packaging films, chemical containers, etc. However, their use as materials for balloon-tip catheters has not been proposed.

The present inventors have carried out an investigation as to whether polyolefins produced using a metallocene catalyst are suitable for materials for forming a balloon of a balloon-tip catheter for dilation or not. As a result, it has been found that balloons excellent in balance among various properties such as shapeability, retention of shape, flexibility and breaking strength compared with low density polyethylene (LDPE) and linear low density polyethylene (LLDPE) obtained by polymerization using the conventional multi-site catalyst such as a Ziegler-Natta catalyst can be provided from them.

By the way, changes in physical properties in a forming and processing step of a balloon and the manner of application of force upon use are extremely complex, and it has also been found that among polyolefins obtained by polymerization using the metallocene catalyst, ethylene-α-olefin copolymers obtained by polymerization using the metallocene catalyst are preferred in order to provide balloons far excellent in such various properties as described above, and ethylene-α-olefin copolymers having a low melting point and high tensile break strength are more preferred. Further, it has been found that when a copolymer having a great difference between the melting point and the softening point and a high ratio of the tensile break strength to the tensile yield strength is selected for use, a balloon markedly improved in such required properties as described above can be provided. The present invention has been led to completion on the basis of these findings.

According to the present invention, there is thus provided a balloon-tip catheter having a balloon formed from a polymeric material in the vicinity of the tip of a catheter, wherein the polymeric material forming the balloon comprises a polyolefin obtained by polymerization using a metallocene catalyst.

BEST MODE FOR CARRYING OUT THE INVENTION

Figure 1:
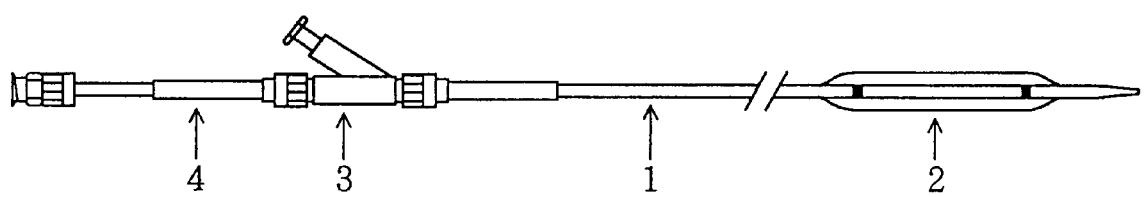
FIG. 1 is a schematic view illustrating an exemplary balloon-tip catheter for dilation.

In the present invention, a polymeric material comprising a polyolefin produced by a polymerization reaction using a metallocene catalyst is used as a material for forming a balloon of a balloon-tip catheter for dilation.

The metallocene catalyst (also referred to as a Kaminsky catalyst or single-site catalyst) is composed of a metallocene compound of a structure that a transition metal is held between unsaturated compounds of a π electron system, and is used in combination with a promotor such as methylaluminoxane or an organoaluminum compound. As examples of the metallocene compound, may be mentioned those containing one or two (substituted) cyclopentadienyl groups, (substituted) indenyl groups, (substituted) tetrahydroindenyl groups or (substituted) fluorenyl groups, or a group obtained by crosslinking 2 groups of these groups by covalent bonding bonded to a transition metal of Group IVA, such as zirconium, titanium or hafnium, and having ligands such as hydrogen atoms, oxygen atoms, halogen atoms, alkyl groups, alkoxy group, aryl groups, acetylacetonato groups, carbonyl groups, nitrogen molecules, oxygen molecules, Lewis bases, silicon atom-containing substituents or unsaturated hydrocarbons. As the promotor, there may also be used a compound which is an ionic or electrophilic compound formed from an ion pair of a cation and an anion and becomes a stable ion by reacting with a metallocene compound to form an active species for polymerization, for example, tetrakis-(pentafluorophenyl)boron.

Examples of a monomer for obtaining the polyolefin by polymerization include ethylene, propylene, 1-butene, 1-pentene, 1-hexene, 1-octene, 1-heptene, 4-methyl-1-pentene, 4-methyl-1-hexene and 4,4-dimethyl-1-pentene. These monomers may be used either singly or in any combination thereof.

The polyolefin is preferably polyethylene or an ethylene-α-olefin copolymer from the viewpoint of various properties of the resulting balloon, with the ethylene-α-olefin copolymer being particularly preferred. The ethylene-α-olefin copolymer can be obtained by copolymerization of ethylene and an α-olefin using a metallocene catalyst. As a comonomer, an α-olefin having 4 to 40 carbon atoms is preferably used. Examples of the α-olefin include 1-butene, 1-pentene, 1-hexene, 1-octene, 1-heptene, 4-methyl-1-pentene, 4-methyl-1-hexene and 4,4-dimethyl-1-pentene. Of these, α-olefins having a 4 to 12 carbon atoms are preferred, with α-olefins having 4 to 10 carbon atoms being particularly preferred. The copolymerization proportion of the α-olefin is generally 2 to 50 wt. %, preferably 5 to 40 wt. %, more preferably 10 to 30 wt. %.

Examples of a (co)polymerization process for obtaining the polyolefin by using the metallocene catalyst include vapor-phase, solution, bulk polymerization, high-pressure and slurry processes. The polymerization is generally conducted under conditions of a polymerization temperature of −100 to 250° C., polymerization time of 5 minutes to 10 hours and a reaction pressure of ordinary pressure to 300 kg/cm$^2$.

The melt flow rate (MFR; JIS K 7210) of a polyolefin such as an ethylene-α-olefin copolymer obtained by polymerization using the metallocene catalyst is generally 0.1 to 30.0 g/10 min, preferably 1.0 to 20.0 g/10 min, more preferably 1.0 to 15.0 g/10 min, most preferably 1.5 to 15.0 g/10 min. If MFR is too low, the resulting balloon is difficult to achieve sufficient strength. If MFR is too high, the forming or molding ability of the polyolefin is deteriorated.

The density (JIS K 7112) of the polyolefin is generally 0.950 g/cm$^3$ or lower, preferably 0.850 to 0.940 g/cm$^3$, more preferably 0.880 to 0.930 g/cm$^3$. If the density is too low, the resulting balloon tends to cause disadvantages such as blocking due to sticking on the surface thereof. If the density is too high, the transparency of the balloon is lowered.

In the polyolefin obtained by polymerization using the metallocene catalyst, the molecular weight distribution is narrow because the metallocene catalyst having an even active site is used, and moreover the composition distribution also becomes narrow in the case of a copolymer such as an ethylene-α-olefin copolymer because the α-olefin as a comonomer is uniformly introduced into the main ethylene chain. Therefore, a component (sticky portion) having a low molecular weight and a low density becomes little, and a component extracted with an organic solvent also becomes little. When a polyethylene resin is used to form a film, spherulites are formed. Units forming the spherulites include a lamella (thin layer like a single crystal). In the ethylene-α-olefin copolymer making use of the metallocene catalyst, the lamella is thin, and on the other hand, tie molecules tying lamellae to each other are present in plenty. These facts permit the formation of a tough film.

The polyolefin making use of the metallocene catalyst, such as the ethylene-α-olefin copolymer, may be synthesized. However, many kinds of polyolefins have been already produced and marketed, and so a marketed product may also be used. Since changes in physical properties in forming and processing of a balloon using a polymeric material and the manner of application of force upon use of the balloon are extremely complex as described above, however, it is desirable to select a polyolefin capable of imparting particularly excellent balloon properties from among the polyolefins obtained by polymerization using the metallocene catalyst. When the polyolefins obtained by polymerization using the metallocene catalyst are used in various application fields, their densities, the kinds and amount of comonomers used, MFR, etc. are used as indices. When they are used as materials for balloons, however, it is not always proper to use these as indices.

The present inventors have carried out an investigation as to various polymeric materials. As a result, it has been found that among polyolefins obtained by polymerization using the metallocene catalyst, polyethylene resins such as polyethylene and ethylene-α-olefin copolymers are preferred in order to provide balloons excellent in processability and moreover in various properties when formed and processed into the balloons, with ethylene-α-olefin copolymers being particularly preferred. As a result of a further investigation, it has also been found that a polyolefin obtained by polymerization using the metallocene catalyst preferably has a melting point of 125° C. or lower and tensile break strength of 250 kg/cm$^2$ or higher, and more preferably has a melting point of 120° C. or lower and tensile break strength of 350 kg/cm$^2$ or higher. In particular, the use of an ethylene-α-olefin copolymer obtained by polymerization using the metallocene catalyst and having a melting point as low as 120° C. or lower and tensile break strength as high as 350 kg/cm$^2$ or higher is most preferable because a balloon far excellent in flexibility and breaking strength and also good in shapeability and retention of shape can be provided.

Accordingly, a polyolefin produced using the metallocene catalyst and having such specific physical properties, particularly, an ethylene-α-olefin copolymer is used as a material for forming a balloon, whereby a balloon high in strength, good in flexibility, capable of designing compliance within a proper range and easy to shape into a balloon and fusion-bond it to a catheter can be provided. The ethylene-α-olefin copolymer contains tie molecules tying lamellae to each other in plenty in proportion to the low melting point and easy forming and processing into a balloon, so that a balloon having high strength can be provided.

In the polyolefins such as the ethylene-α-olefin copolymers produced using the metallocene catalyst, a difference (melting point–softening point) between the melting point and the softening point is preferably at least 15° C. When a polyolefin great in the difference between the melting point and the softening point and low in softening point is used, the shaping of the resulting balloon is easy when the balloon is folded, and its setting ability becomes good. The balloon-tip catheter for dilation is shaped into, for example, a fixed form that a balloon is wound around a catheter in order to facilitate its insertion into and extraction from a coeloma such as a vessel, and the fixed form is often retained while the balloon is deflated under reduced pressure. However, low density polyethylene (LDPE), which is the conventional material for balloon, is low in melting point, but relatively high in softening point and is not always sufficient in shapeability and retention of shape. Linear low density polyethylene (LLDPE) obtained by polymerization using the conventional multi-site catalyst is great in a difference between the melting point and the softening point, but high in melting point and also relatively high in softening point. Therefore, its shapeability and retention of shape are insufficient.

In the polyolefins such as the ethylene-α-olefin copolymers produced using the metallocene catalyst, a ratio of the tensile break strength (TB) to the tensile yield strength (Tγ) is preferably at least 3.0 times. Since the polyolefins such as the ethylene-α-olefin copolymers having such physical properties have high tensile break strength and moreover a high ratio of the tensile break strength to the tensile yield strength compared with, for example, the conventional polyethylene resins, they are easy to be stretched upon the forming and processing of balloons and hence to gain the effect of the stretching. The ethylene-α-olefin copolymers obtained by polymerization using the metallocene catalyst are narrow in molecular weight distribution and excellent in uniform stretchability. However, with respect to those produced using a process comprising subjecting a tubular parison to stretch blow molding, like a balloon, the stretching tends to become uneven due to the thickness irregularity of the tube. However, an ethylene-α-olefin copolymer having a ratio of the tensile break strength to the tensile yield strength of at least 3.0 times is extremely low in tensile yield strength compared with the tensile break strength. Therefore, even when a balloon is formed from such a copolymer by, for example, stretch blow molding, and thickness irregularity is present in a tubular parison, uniform stretching can be performed over the whole balloon. In addition, since the tensile break strength is high, a high-quality and high-strength balloon is provided.

Further, when a polyolefin such as an ethylene-α-olefin copolymer having a high ratio of the tensile break strength to the tensile yield strength is used, a balloon having a compliance (rate of change in the diameter of the balloon inflated to the dilation pressure of the balloon) upon inflation of the balloon within a proper range, for example, it being low compared with the conventional polyethylene resins, and on the other hand being high compared with polyester resins and polyamide resins, can be provided. If the compliance is too high, it is difficult to stably dilate a vessel. If the compliance is too low, it is difficult to efficiently dilate the vessel.

The balloon according to the present invention is excellent in flexibility in spite of high strength due to even molecular weight, small and even thin spherulite layer (lamella) and high presence probability of tie molecules tying these lamellae to each other, which are characteristic of the polyolefin such as the ethylene-α-olefin copolymer obtained using the metallocene catalyst, so that a balloon which is not stiff even when it is deflated under reduced pressure can be provided. On the other hand, the use of a polymeric material of the polyamide or polyester type, the molecular chain of which is high in crystallinity, results in a stiff balloon.

In the present invention, the polymeric material forming the balloon comprises a polyolefin obtained by polymerization using the metallocene catalyst, particularly preferably, an ethylene-α-olefin copolymer having the following features:

(1) the melting point being 120° C. or lower;

(2) the tensile break strength being at least 350 kg/cm$^2$;

(3) a difference between the melting point and the softening point being at least 15° C.; and (4) a ratio (TB/Tγ) of the tensile break strength (TB) to the tensile yield strength (Tγ) being at least 3.0.

The melting point of the ethylene-α-olefin copolymer is preferably within a range of 95 to 120° C., more preferably 100 to 120° C. The softening point thereof is preferably within a range of 70 to 105° C., more preferably 75 to 103° C. The difference between the melting point and the softening point is preferably within a range of 15 to 50° C., more preferably 15 to 45° C. The tensile break strength is preferably within a range of 350 to 500 kg/cm$^2$, more preferably 355 to 450 kg/cm$^2$. The ratio (TB/Tγ) of the tensile break strength (TB) to the tensile yield strength (Tγ) is preferably within a range of 3.0 to 10.0, more preferably 3.5 to 8.0.

In the present invention, the polyolefin obtained by polymerization using the metallocene catalyst, particularly preferably, the above-described specific ethylene-α-olefin copolymer may be used by itself as the polymeric material for forming the balloon. However, various kinds of additives, and other resins and elastomers may be incorporated so far as no detrimental influence is thereby imposed on the object of the present invention.

As the additives, several of, for example, antioxidants, ultraviolet absorbents, antistatic agents, flame retardants, metal deactivators, pigments, dyes, nucleating agents, etc. may be added as needed. In this case, the amount added is generally 20 parts by weight or less, preferably 5 parts by weight or less per 100 parts by weight of the polyolefin though it varies according to the required properties of the resulting balloon.

Examples of other resins include various resins obtained by polymerization using a Ziegler-Natta catalyst, for example, polyolefin resins such as polypropylene resins, high density polyethylene, linear low density polyethylene, ultra low density polyethylene, high-pressure-processed low density polyethylene, ethylene-vinyl acetate copolymers, ethylene-acrylic ester copolymers, ethylene-acrylic acid copolymers, ethylene-methacrylic acid copolymers and ethylene-carbon monoxide copolymers; and various kinds of thermoplastic resins such as amorphous polystyrene resins, crystalline polystyrene resins, polyvinyl chloride resins, polyamide, polyacetal and polycarbonate. The blending proportion of these other resins is generally 100 parts by weight or lower, preferably 50 parts by weight or lower, more preferably 30 parts by weight or lower per 100 parts by weight of the polyolefin.

As the elastomers, there may be used, for example, solid rubbers such as ethylene-propylene rubber, ethylene-1-butene rubber, propylene-l-butene rubber, styrene-butadiene rubber and hydrogenated products thereof, isoprene rubber, neoprene rubber, and acrylonitrile-butadiene rubber and hydrogenated products thereof; styrene type thermoplastic elastomers such as styrene-butadiene block copolymer elastomers and hydrogenated products thereof; and other various elastomers. The blending proportion of the elastomers is generally 100 parts by weight or lower, preferably 50 parts by weight or lower, more preferably 30 parts by weight or lower per 100 parts by weight of the polyolefin.

In the present invention, mixing of other components into the polyolefin is conducted by liquid mixing or solid mixing. However, melt mixing are generally used. For example, any of various kneaders such as rolls, screw mixers, Banbury mixer, kneaders, blenders and mills is used to knead the respective components at a desired temperature, and the kneaded mixture is then pelletized into particles of a proper size. In this case, any process of strand cut process, underwater cut process, hot cut process, mist cut process, sheet cut process, freeze grinding process and melt spraying process may be used.

As a process for forming a balloon from the polymeric material comprising the polyolefin, a process comprising preparing a tubular parison in accordance with a method known per se in the art and subjecting the tubular parison to stretch blow molding in a mold is adopted. An extrusion process, a copper wire coating process or the like is adopted for the formation of the tubular parison. The temperature of the blow molding is generally about 30 to 180° C., preferably about 80 to 120° C. The draw ratio in a machine direction is preferably controlled to at least 130%, and the effective total draw ratio (sectional area of tube/sectional area of balloon) is preferably controlled to at least 5 times. After stretch blow molding, a heat treatment may be conducted to prevent the resulting balloon from causing great heat shrinkage by subsequent heat history.

The tubular parison may be subjected to stretch blow molding as it is, or if desired, after crosslinking it by irradiation of ionizing radiation such as electron beams. The pressure resistance of the balloon can be improved by the radiation crosslinking. The irradiation dose is generally about 2 to 15 MR. The gel fraction of the tube crosslinked by the irradiation is preferably controlled to generally about 0.75 to 0.95. The gel fraction can be determined as insoluble matter in heated xylene contained in a crosslinked sample. More specifically, 0.1 g of the crosslinked sample is heated for 6 hours in 100 ml of xylene heated to 120° C., soluble matter is then separated by filtration, and the dry weight of the remaining crosslinked sample is measured to calculate out its proportion to the crosslinked sample before the treatment.

The balloon thus obtained may be used as it is, and another layer such as a polyurethane coating may be laminated thereon if desired. Besides, the surface of the balloon may also be coated with any of various kinds of natural or synthetic hydrophilic polymers to enhance the lubricity of the balloon in blood or a physiological saline.

In the present invention, the polymeric material comprising the polyolefin obtained by polymerization using the metallocene catalyst, preferably, the specific ethylene-α-olefin copolymer is used as a material for forming a balloon. Therefore, a thin balloon excellent in processability into a balloon and high in strength can be provided. This balloon is good in shapeability, retention of shape, flexibility and the like, and its compliance also falls within a proper range. The balloon is also excellent in fusion-bonding ability to a catheter. Accordingly, the use of this balloon permits the provision of a balloon-tip catheter for dilation satisfying the highly required properties. The size of the balloon may be suitably determined according to a site applied. In the case of a balloon-tip catheter for vasodilation, however, the length is about 10 to 100 mm, and the outer diameter is about 2 to 10 mm. The film thickness of the balloon is generally about 5 to 100 $\mu$m, preferably about 10 to 50 $\mu$m. When the catheter is applied to a peripheral coronary artery, however, the balloon may be made low profile.

The balloon-tip catheters according to the present invention have a balloon formed from the polymeric material comprising the polyolefin obtained by polymerization using the metallocene catalyst in the vicinity of the tip of a catheter. A typical example thereof illustrates in FIG. 1. As examples of the material of the catheter, may be mentioned general-purpose polymeric materials such as high density polyethylene, polyvinyl fluoride and polyimide. However, the same polyolefin obtained by polymerization using the metallocene catalyst as that used in the balloon may be used.

EXAMPLES

The present invention will hereinafter be described more specifically by the following Examples and Comparative Examples.

Examples 1 to 6 and Comparative Examples 1 to 4
(1) Forming and Processing of Balloon:

Respective resins having their corresponding material characteristics shown in Tables 1 and 2 were used as materials for forming balloons to produce raw tubes each having an outer diameter of about 1 mm and a wall thickness of 50 $\mu$m by extrusion. Each of the raw tubes was cut into lengths of 100 mm to prepare a tubular parison. The tubular parison was placed in an outer mold for balloon having an inner diameter 4 mm and a length of 30 mm to conduct blow molding under conditions that a molding temperature is preset within a range from 0.5 to 0.8 times of the melting point of each resin, and a molding pressure within 8±4 kg/cm$^2$, and the blown parison was stretched in a radial direction, thereby forming and processing a balloon.

(2) Fusion Bonding of Balloon:

Each balloon formed and processed above was fusion-bonded to a catheter tube (made of polyethylene) having an outer diameter of 1 mm and a wall thickness of 200 $\mu$m. The fusion-bonding temperature was controlled to (the melting point of each resin ±0.2° C.).

(3) Shaping of Balloon:

Each balloon-tip catheter produced above was placed under reduced pressure to wind the balloon in the circumferential direction of the catheter, and the balloon-tip catheter was then covered with a sheath for retaining the shape to conduct shaping at 70° C. for 1 hour.

(4) Evaluation of Properties:

After the shaping step, the balloon-tip catheter was taken out of the sheath to evaluate its properties. (n=30)

① Shapeability:

After the sheath was removed, the form of the balloon under reduced pressure was observed to evaluate the shapeability in accordance with the following standard:

○: The balloon was completely wound around the catheter;

Δ: The winding form of the balloon was somewhat disordered; and

X: The winding form of the balloon was disordered.

② Retention of shape:

The balloon was inflated and deflated again under reduced pressure to observe the form of the balloon, thereby evaluating the retention of shape in accordance with the following standard:

○: The balloon was completely wound around the catheter;

Δ: The winding form of the balloon was somewhat disordered; and

X: The winding form of the balloon was disordered.

③ flexibility:

After the sheath was removed, the balloon under reduced pressure was held between fingers to evaluate the flexibility from its hardness in accordance with the following standard:

○: Felt flexible and soft;

Δ: Felt somewhat hard; and

X: Felt hard and stiff.

④ Breaking strength:

An internal pressure was applied to balloons to measure a pressure under which at least 90% of the balloons were not broken.

TABLE 1

| | Example | | | | | |
|---|---|---|---|---|---|---|
| | 1 | 2 | 3 | 4 | 5 | 6 |
| | Metallocene-catalyzed ethylene-α-olefin copolymer | | | | | |
| Material for balloon | A | B | C | D | E | F |
| Material Characteristics: | | | | | | |
| Tensile break strength $T_B$ [kg/cm$^2$] | 400 | 400 | 360 | 360 | 350 | 270 |
| Tensile yield strength $T_\gamma$ [kg/cm$^2$] | 57 | 56 | 105 | 100 | 140 | 60 |
| $T_B/T_\gamma$ | 7.0 | 7.1 | 3.4 | 3.6 | 2.5 | 4.5 |
| Melting point [° C.] | 113 | 103 | 117 | 113 | 121 | 108 |
| Softening point [° C.] | 79 | 81 | 101 | 98 | 110 | 75 |
| (Melting point - Softening point) [° C.] | 34 | 22 | 16 | 15 | 11 | 33 |
| Hardness | 45 | 45 | 55 | 54 | 56 | 43 |
| Forming and processing of balloon: | | | | | | |
| Molding temperature [° C.] | 80 | 73 | 83 | 80 | 88 | 77 |
| Molding pressure [kg/cm] | 6.7 | 6.1 | 7.0 | 6.7 | 7.2 | 6.5 |
| Fusion-bonding temperature [° C.] | 112 | 102 | 115 | 112 | 122 | 109 |
| Shaping temperature [° C.] | 70 | 70 | 70 | 70 | 70 | 70 |
| Balloon size: | | | | | | |
| Outer diameter [mm] | 4.0 | 4.0 | 4.0 | 4.0 | 4.0 | 4.0 |
| Filmn thickness [$\mu$m] | 24 | 24 | 24 | 24 | 24 | 24 |
| Length [mm] | 30 | 30 | 30 | 30 | 30 | 30 |
| Evaluation of balloon: | | | | | | |
| Shapeability | ○ | ○ | ○ | ○ | Δ | Δ |
| Retention of shape | ○ | ○ | ○ | ○ | Δ | Δ |
| Flexibility | ○ | ○ | ○ | ○ | Δ | Δ |
| Break strength [kg/cm$^2$] | 20 | 20 | 18 | 18 | 10 | 10 |

TABLE 2

|  | Comparative Example | | | |
|---|---|---|---|---|
|  | 1 | 2 | 3 | 4 |
|  | | LLDPE | | |
| Material for balloon | ① | ② | ③ | LDPE |
| Material characteristics: | | | | |
| Tensile break strength $T_B$ [kg/cm$^2$] | 390 | 390 | 300 | 215 |
| Tensile yield strength $T_\gamma$ [kg/cm$^2$] | 140 | 130 | 110 | 105 |
| $T_B/T_\gamma$ | 2.7 | 3.0 | 2.7 | 2.0 |
| Melting point [° C.] | 127 | 127 | 124 | 111 |
| Softening point [° C.] | 108 | 105 | 102 | 98 |
| (Melting point - Softening point) [° C.] | 19 | 22 | 22 | 13 |
| Hardness | 61 | 56 | 55 | 51 |
| Forming and processing of balloon: | | | | |
| Molding temperature [° C.] | 80 | 90 | 88 | 79 |
| Molding pressure [kg/cm] | 7.6 | 7.6 | 7.4 | 6.6 |
| Fusion-bonding temperature [° C.] | 129 | 129 | 125 | 113 |
| Shaping temperature [° C.] | 70 | 70 | 70 | 70 |
| Balloon size: | | | | |
| Outer diameter [mm] | 4.0 | 4.0 | 4.0 | 4.0 |
| Film thickness [μm] | 24 | 24 | 24 | 24 |
| Length [mm] | 30 | 30 | 30 | 30 |
| Evaluation of balloon: | | | | |
| Shapeability | Δ | Δ | Δ | Δ |
| Retention of shape | X | X | X | Δ |
| Flexibility | X | X | Δ | Δ |
| Break strength [kg/cm$^2$] | 10 | 9 | 9 | 6 |

Measuring Method
Tensile Break Strength and Tensile Yield Strength

A test was made by means of an Instron type tensile tester in accordance with JIS K 7127-1989. The tensile break strength means tensile stress at break of a specimen, and the tensile yield strength means stress corresponding to the first point at which increase in elongation is observed without increase in load on a load-elongation curve.

Resins Used:
(1) Resin A: an ethylene-1-hexene copolymer (density= 0.905 g/cm$^3$, MFR=2.2 g/10 min),
(2) Resin B: an ethylene-1-hexene copolymer (density= 0.910 g/cm$^3$, MFR=3.5 g/10 min),
(3) Resin C: an ethylene-1-hexene copolymer (density= 0.917 g/cm$^3$, MFR=2.0 g/10 min),
(4) Resin D: an ethylene-1-hexene copolymer (density= 0.915 g/cm$^3$, MFR=4.0 g/10 min),
(5) Resin E: an ethylene-1-hexene copolymer (density= 0.928 g/cm$^3$, MFR=2.0 g/10 min),
(6) Resin F: an ethylene-1-hexene copolymer (density= 0.905 g/cm$^3$, MFR=11.0 g/10 min),
(7) LLDPE ①: (density=0.926 g/cm$^3$, MFR=0.8 g/10 min),
(8) LLDPE ②: (density=0.926 g/cm$^3$, MFR=0.3 g/10 min),
(9) LLDPE ③: (density=0.924 g/cm$^3$, MFR=0.3 g/10 min),
(10) LDPE: (density=0.923 g/cm$^3$, MFR=0.25 g/10 min).

As apparent from the results shown in Tables 1 and 2, the balloon-tip catheters according to the present invention are good in balloon properties. In particular, the balloons formed with an ethylene-α-olefin copolymer obtained by polymerization using the metallocene catalyst and having a melting point of 120° C. or lower, tensile break strength of 350 kg/cm$^2$ or higher, a difference between the melting point and the softening point of at least 15° C and a ratio of the tensile break strength to the tensile yield strength of at least 3.0 times were such that the shapeability, retention of shape, flexibility and breaking strength are markedly excellent, their compliance falls within a proper range, and a vessel can be safely and efficiently dilated. Accordingly, the balloon-tip catheters according to the present invention are particularly suitable for use as balloon-tip catheters for dilation.

INDUSTRIAL APPLICABILITY

According to the present invention, there are provided balloon-tip catheters having a balloon which is high in strength, excellent in flexibility, easy to shape the balloon when it is folded, good in setting ability, has a compliance within a proper range when it is inflated, and moreover is excellent in processability, retention of shape and fusion-bonding ability to a catheter, and being suitable for use as balloon-tip catheters for dilation.

What is claimed is:

1. A balloon-tip catheter having a balloon formed from a polymeric material in the vicinity of the tip of a catheter, wherein the polymeric material forming the balloon comprises an ethylene-α-olefin copolymer obtained by polymerization using a metallocene catalyst.

2. The balloon-tip catheter according to claim 1, wherein the ethylene-α-olefin copolymer is a copolymer of ethylene and an α-olefin having 4 to 40 carbon atoms.

3. The balloon-tip catheter according to claim 2, wherein the ethylenie-α-olefin copolymer has a melting point of 125° or lower and tensile break strength of 250 kg/cm$^2$ or higher.

4. The balloon-tip catheter according to claim 2, wherein the ethylene-α-olefin copolymer has a melting point higher by at least 15° C. than the softening point thereof.

5. The balloon-tip catheter according to claim 2, wherein the ethylenc-α-olefin copolymer has a ratio of the tensile break strength to the tensile yield strength of at least 3.0 times.

6. The balloon-tip catheter according to claim 2, wherein the ethylene-α-olefin copolymer is a copolymer of ethylene and an α-olefin having 4 to 12 carbon atoms.

7. The balloon-tip catheter according to claim 1, wherein the ethylene-α-olefin copolymer has a melting point of 125° C. or lower and tensile break strength of 250 kg/cm$^2$ or higher.

8. The balloon-tip catheter according to claim 7, wherein the ethylene-α-olefin copolymer has a melting point of 120° C. or lower and tensile break strength of 350 kg/cm$^2$ or higher.

9. The balloon-tip catheter according to claim 1, wherein the ethvlene-α-olefin copolymer has a melting point higher by at least 15° than the softening point thereof.

10. The balloon-tip catheter according to claim 1, wherein the ethylene-α-olefin copolymer has a ratio of the tensile break strength to the tensile yield strength of at least 3.0 times.

11. The balloon-tip catheter according to claim 1, wherein the ethylene-α-olefin copolymer is an ethylene-u-olefin copolymer having the following features:
(1) the melting point being 120° C. or lower;
(2) the tensile break strength being at least 350 kg/cm$^2$;
(3) a difference between the melting point and the softening point being at least 15° C.; and
(4) a ratio (TB/Tγ) of the tensile break strength (TB) to the tensile yield strength (Tγ) being at least 3.0.

12. The balloon-tip catheter according to claim 1, which is a balloon-tip catheter for dilation.

* * * * *

UNITED STATES PATENT AND TRADEMARK OFFICE
CERTIFICATE OF CORRECTION

PATENT NO. : 6,238,408 B1
DATED : May 29, 2001
INVENTOR(S) : Takashi Kawabata et al.

It is certified that error appears in the above-identified patent and that said Letters Patent is hereby corrected as shown below:

<u>Column 12, claim 3,</u>
Line 29, change "125°" to -- 125°C --.

<u>Column 12, claim 9,</u>
Line 50, change "15°" to -- 15°C --.

<u>Column 12, claim 11,</u>
Line 56, change "ethylene-u-olefin" to -- ethylene-α-olefin --.

Signed and Sealed this

Sixteenth Day of April, 2002

Attest:

JAMES E. ROGAN
Attesting Officer *Director of the United States Patent and Trademark Office*